US010768259B2

(12) United States Patent
Taher et al.

(10) Patent No.: US 10,768,259 B2
(45) Date of Patent: Sep. 8, 2020

(54) CEREBROVASCULAR SEGMENTATION FROM MRA IMAGES

(71) Applicant: Zayed University, Dubai (AE)

(72) Inventors: Fatma Taher, Dubai (AE); Ayman S. El-Baz, Louisville, KY (US)

(73) Assignee: ZAYED UNIVERSITY, Dubai (AE)

( * ) Notice: Subject to any disclaimer, the term of this patent is extended or adjusted under 35 U.S.C. 154(b) by 138 days.

(21) Appl. No.: 16/159,790

(22) Filed: Oct. 15, 2018

(65) Prior Publication Data

US 2020/0116808 A1 Apr. 16, 2020

(51) Int. Cl.
*G01R 33/563* (2006.01)
*A61B 5/055* (2006.01)
(Continued)

(52) U.S. Cl.
CPC .......... *G01R 33/5635* (2013.01); *A61B 5/055* (2013.01); *G01R 33/56316* (2013.01); *G06T 7/162* (2017.01); *A61B 5/02014* (2013.01); *A61B 5/0263* (2013.01); *A61B 2576/026* (2013.01); *G01R 33/5602* (2013.01);
(Continued)

(58) Field of Classification Search
CPC .................. G06T 7/0012; G06T 7/143; G06T 2207/30016; G06T 2207/20224; G06T 2207/30104; G06T 5/50; G06T 7/162; A61B 2576/026; A61B 5/02014;
(Continued)

(56) References Cited

U.S. PATENT DOCUMENTS 9,014,456 B2 * 4/2015 El-Baz .................. G06K 9/621
  382/133
9,501,620 B2 * 11/2016 Okell ..................... A61B 6/507
(Continued)

OTHER PUBLICATIONS

Razlighi et al, "Causal Markov Random Field for Brain MR Image Segmentation", Aug. 28-Sep. 1, 2012, 34th Annual International Conference of the IEEE EMBS, pp. 1-4. (Year: 2012).*
(Continued)

*Primary Examiner* — Margaret G Mastrodonato
(74) *Attorney, Agent, or Firm* — Hayes Soloway PC

(57) ABSTRACT

There is provided a method of processing a cerebrovascular medical image, the method comprising receiving magnetic resonance angiography (MRA) image associated with a cerebrovascular tissue comprising blood vessels and brain tissues other than blood vessels; segmenting MRA image using a prior appearance model for generating first prior appearance features representing a first-order prior appearance model and second appearance features representing a second-order prior appearance model of the cerebrovascular tissue, wherein current appearance model comprises a 3D Markov-Gibbs Random Field (MGRF) having a 2D rotational and translational symmetry such that MGRF model is 2D rotation and translation invariant; segmenting MRA image using current appearance model for generating current appearance features distinguishing blood vessels from other brain tissues; adjusting MRA image using first and second prior appearance features and current appearance futures; and generating an enhanced MRA image based on said adjustment. There is also provided a system for doing the same.

22 Claims, 5 Drawing Sheets

(51) Int. Cl.
*G06T 7/162* (2017.01)
*G06T 5/50* (2006.01)
*A61B 5/026* (2006.01)
*A61B 5/02* (2006.01)
*G01R 33/56* (2006.01)

(52) U.S. Cl.
CPC ...... *G06T 5/50* (2013.01); *G06T 2207/20224* (2013.01); *G06T 2207/30016* (2013.01); *G06T 2207/30104* (2013.01)

(58) Field of Classification Search
CPC .. A61B 5/0263; A61B 5/055; G01R 33/5602; G01R 33/56316; G01R 33/5635
See application file for complete search history.

(56) References Cited

U.S. PATENT DOCUMENTS

| | | | | |
|---|---|---|---|---|
| 2010/0111386 A1* | 5/2010 | El-Baz | ............... | G06T 7/33 382/128 |
| 2013/0259346 A1* | 10/2013 | El-Baz | ............... | G06T 7/0012 382/131 |
| 2013/0294669 A1* | 11/2013 | El-Baz | ............... | G06T 5/002 382/131 |
| 2018/0070905 A1* | 3/2018 | El-Baz | ............... | G06T 7/149 |
| 2019/0237186 A1* | 8/2019 | El-Baz | ............... | G16H 30/40 |
| 2019/0279358 A1* | 9/2019 | Schaal | ............... | G06T 7/168 |

OTHER PUBLICATIONS

El-Baz et al, "3D Joint Markov-Gibbs Model for Segmenting the Blood Vessels From MRA", 2009 IEEE International Symposium on Biomedical Imaging: From Nano to Macro, pp. 1-4 (Year: 2009).*

Cao et al, "A parallel Markov cerebrovascular segmentation algorithm based on statistical model", Mar. 2016, Journal of Computer Science and Technology 31(2): pp. 400-416 (Year: 2016).*

Kandil et al, "A Novel MRA Framework Based on Integrated Global and Local Analysis for Accurate Segmentation of the Cerebral Vascular System", 2018 IEEE 15th International Symposium on Biomedical Imaging (ISBI 2018), pp. 1-4 (Year: 2018).*

Lv et al, "Cerebrovascular Segmentation Algorithm Based on Focused Multi-Gaussians Model and Weighted 3D Markov Random Field", 2019 IEEE International Conference on Bioinformatics and Biomedicine (BIBM), pp. 1-6 (Year: 2019).*

Roche et al, "On the convergence of EM-like algorithms for image segmentation using Markovrandom fields", 2011, Elsevier Medical Image Analysis, vol. 15, Issue 6, pp. 830-839 (Year: 2011).*

* cited by examiner

Average Vessel Volume Difference (AVVD)

CEREBROVASCULAR SEGMENTATION FROM MRA IMAGES

FIELD OF THE INVENTION

The present invention relates to the field of medical diagnostics, and more particularly to a method and system for processing cerebrovascular medical images.

BACKGROUND OF THE INVENTION

In medicine, there are some diseases that have complicated nature and should be analysed deeply in order to provide the patient with the right treatment. Among these diseases that can lead to death, or disability are the cerebrovascular diseases. These types of diseases commonly occur due to the dysfunction of the blood vessels supplying the brain. There are different kinds of cerebrovascular diseases including aneurysms, strokes, arteriovenous malformation, and carotid stenosis. Haemorrhage, a cerebrovascular disease, is considered a cause for strokes for almost 20% of the cases. Furthermore, cerebrovascular diseases are considered the third leading cause of death and disability. For neurosurgeons, analysing the brain scans manually takes a long time and a lot of effort especially when tracking a small vessel in the orthogonal view in order to be able to get a better picture of the vascular anatomy. With the aid of bio-engineers and computer engineers, several computer aided diagnostic (CAD) systems have been developed to analyse cerebrovascular structures, taking into consideration that any CAD system needs accurate segmentation of the cerebrovasculature from the surroundings, and this is the main motivation behind developing our approach.

Several modalities have been used for non-invasive vascular imaging e.g., computed tomography angiography (CTA) and magnetic resonance angiography (MRA). The three commonly used MRA techniques are Time-of-Flight MRA (TOF-MRA), phase contrast angiography (PCA), and contrast enhanced MRA (CE-MRA). Both TOF-MRA and PCA use flowing blood as an inherent contrast medium, while for CE-MRA a contrasting substance is injected into the circulatory system. PCA exploits phase changes of transverse magnetization when flowing spins move through a magnetic field gradient. This provides good background signal suppression and can quantify flow velocity vectors for each voxel. TOF-MRA relying on amplitude differences in longitudinal magnetization between flowing static spins is less quantitative, however it is fast and provides high contrast images. The fact that it is widely used in clinical practice is another motivation behind our work. An overview of the most recent approaches for vascular segmentation will be given below, focusing on cerebrovascular approaches using MRA, which are mainly categorized in literature into scalespace filtering, centerline-based, deformable, statistical, and hybrid models.

Multiscale filters improve the curvilinear structures in 3D medical imaging by using multiple scales to convolve an image with Gaussian filters. Moreover, analyzing the eigenvalues of the Hessian for each voxel determines the 3D structures local shapes. The output of the multiscale filtering represents a new enhanced image in a manner that makes curvilinear structures look brighter while other components look darker. A multiscale-based approach was proposed in a prior art in which Markov marked point processes are used for extracting coronary arteries in 2D X-ray angiograms. The Coronary vessels are locally modelled as piece-wise linear segments of variable widths, lengths, locations, and orientations. A Markov object process based on a uniform Poisson process is used to extract the centerlines of the vessels. In order to optimize the process, simulated annealing is done using a reversible Markov chain Monto Carlo technique.

Minimal path centerline-based approaches formulate the extraction of the centerline using 2 points as the minimum cost integrated across the path of the centerline. The centerlines of blood vessels were extracted by G¨uls¨un and Tek by computing the graph edge cost in the direction of the minimal path using medialness multiscale filtering. The centerline of the full vessel tree was then extracted using a post processing algorithm based on the centerlines scale and length. Furthermore, another prior art proposed a framework for extracting the tubular structures automatically from 2D images using the shortest paths. They merged orientation and multiscale optimization for the 4D paths to be propagated on the 2D images, where 4D refers to the combination of scale, space and orientation. Minimal path approaches could result in shortcut problems by tracking a false straight path instead of the true curve. This problem was handled by traditional methods, which segmented the coronary arteries using a minimum average-cost path.

For deformable models based segmentation techniques or active contour models (ACM), they mainly tend to find an estimate of the blood vessels boundary surface. The surface energy is optimized by the evolution of an initial boundary (snake). This is dependent on the smoothness of the surface, in addition to the image gradients. Traditional systems developed a maximum intensity projection (MIP) active contour based approach for cerebrovascular segmentation. Their method projects the brain into 2D space where an integrated ACM is applied, and the output is then converted back into 3D. Although the results of this method were very promising, it is complicated as it requires a lot of projections. To segment complex objects and obtain the energy function, it is preferable to consider both the region information and boundary information. A hybrid level-set (HLS) has been previously proposed by prior art for brain segmentation. A threshold value was set which represented the lower gray boundary so the algorithm will only extract the image parts with a gray level that is higher than the defined threshold. However, the used threshold value was constant which cannot fit different intensity distributions. Hong et al. proposed a localized hybrid level-set (LLS) that calculates the dynamic threshold locally for the targeted object in the image. Their method was found to segment small vessels more effectively but loses the information in the thick parts. Thus, the HLS was more effective in segmenting thick vessels but not in tiny vessels, whereas the LLS was more effective in extracting tiny vessels.

When comparing deformable models to scale space filtering, deformable models give better results, however they might require some human interaction represented in the initialization. Also, it is worth mentioning that deformable models and scale space filtering are slower than statistical methods.

Statistical approaches for extracting blood vessels are automatic, however the accuracy depends on the probability models being involved. The MRA scans can be considered multimodal as the intensities of each region are accompanied with a specific dominant mode of the intensity total marginal probability distribution. For adaptive statistical vascular segmentation approaches, they were introduced by prior art for TOF-MRA for PC-MRA. In the marginal data distribution was represented with a mixture of 2 Gaussians in addition to a uniform component, corresponding respectively to brain tissues, cerebrospinal fluid, and arteries, while Rician distributions were used in instead of Gaussians. Both approaches made use of a conventional expectation maximization (EM) algorithm in order to estimate the parameters of the mixture. Such EM algorithm was modified in by using the marginal grey level distribution instead of the actual grey levels. This modification has been commonly known for density estimation.

Various hybrid techniques worked on combining the previously mentioned techniques. As an example, prior art combined shape information and signal statistics to derive a region-based deformable contour to segment tubes. Furthermore, geometry of surfaces and second order statistics were used by prior art to guide a deformable model surface for the purpose of vascular segmentation in PC-MRA and TOF-MRA. Traditional systems proposed a method based on a Rayleigh-Gaussian mixture model. In their method, when analyzing the histogram, many nonvascular voxels are removed, therefore, this problem can be avoided by dividing the voxels based on their region where vascular voxels are in regions with high intensity and non-vascular voxels are found in the low intensity regions. Prior art proposed a segmentation method that was based on Markov random field (MRF) and particle swarm optimization (PSO) algorithms. In addition, a new finite mixture mode with two Gaussian and one Rayleigh distributions used for the intensity histogram of brain tissues in medical image. Traditional methods presented a cerebrovascular segmentation framework from TOF-MRA that combines statistical, deformable and scale-space techniques. In these methods, they calculated the vesselness and then used fuzzy logic to combine it with the TOF-MRA data.

This was then used to initialize a level-set technique. This work was extended by prior art by modifying the vesselness function to include multiscaling in order to handle different vascular sizes. Moreover, a traditional system proposed a framework for segmenting cerebral vessels from MRA using gradient information and statistics.

In summary, traditional methods demonstrate the following limitations:
- Most of them are semiautomatic which require user interaction to initialize a vessel of interest, in particular, the deformable based segmentation approaches.
- Some of them developed their approaches based on an assumption the vessels follow tubular shape; this holds for healthy people but not for patients with stenosis or an aneurysm.
- Most of them are developed based on using pretrained models and did not take into account any features from the given data to make their approach adaptable and not biased to the training data.

SUMMARY OF THE INVENTION

Therefore, in order to overcome at least a part of the shortcomings of the prior art, there exists a need to develop a method of processing a cerebrovascular medical image.

It is an object of the present invention to develop a method of processing a cerebrovascular medical image, the method comprising receiving a magnetic resonance angiography (MRA) image associated with a cerebrovascular tissue comprising blood vessels and brain tissues other than blood vessels, segmenting the MRA image using a prior appearance model for generating first prior appearance features representing a first-order prior appearance model and second appearance features representing a second-order prior appearance model of the cerebrovascular tissue, wherein the current appearance model comprises a 3D Markov-Gibbs Random Field (MGRF) having a 2D rotational and translational symmetry such that the MGRF model is 2D rotation and translation invariant, segmenting the MRA image using a current appearance model for generating current appearance features distinguishing the blood vessels from the other brain tissues, adjusting the MRA image using the first and second prior appearance features and the current appearance futures and generating an enhanced MRA image based on said adjustment.

In an embodiment of the invention, the prior appearance model uses interaction parameters analytically estimated from a set of MRA training data.

In an embodiment of the invention, the first prior appearance features representing a first-order prior appearance model and the second appearance features representing a second-order prior appearance model are respectively provided by energies of the training data according to the following equations:

$$E_0(z) = \sum_{q=0}^{Q-1} F_{0,vasc}(q; z)[F_{0,vasc}(q; z) - 1]$$

$$E_v(z) = \sum_{q=0}^{Q-1} \sum_{q'=0}^{Q-1} F_{v,vasc}(q; q'; z)[F_{v,vasc}(q; q'; z) - 1]$$

wherein, $E_0$ and $E_v$: variances of the co-occurrence distributions are used as a discriminatory features that represent the first order and second-order prior appearance model of cerebral vasculature $F_{0,vasc}$: marginal empirical distributions of gray levels $F_{v,vasc}$: gray level co-occurrences and describe all the cerebral vasculature from the training data.

In an embodiment of the invention, the prior appearance model excludes alignment of the training data. This being said, the model does not require any alignment stage.

In an embodiment of the invention, the current appearance model comprises a Linear combination of Discrete Gaussians (LCDG) model and an EM-based model for linear combination of Gaussian approximation.

In an embodiment of the invention, the generating current appearance features comprises estimating first Gibbs probability densities of voxels to be blood vessels (P (q Vessels)) and estimating second Gibbs probability densities of voxels to be brain tissues other than blood vessels (P (q Brain)) according to the following equations respectively and making probabilistic decisions based on said first and second calculated Gibbs probability densities:

$$P(q|\text{Brain}) = \frac{1}{\alpha} \sum_{r=1}^{2} wp, r\psi(q|\theta p, r) - \sum_{l=1}^{C_n} w_{n,l} \psi(q|\theta_{n,l})$$

$$P(qVessels) = \frac{1}{1-\alpha} \sum_{r=3}^{C_p} wp, r\psi(q|\theta p, r) - \sum_{l=1}^{C_n} w_{n,l} \psi(q|\theta_{n,l})$$

$$\text{Where } \alpha = \frac{wp, 1 + wp, 2}{\sum_r w_{p,r}}$$

wherein $C_p$, $C_n$, $w_p$, $w_n$, $\theta_p$, $\theta_n$ denotes the parameters of the LCDG.

In an embodiment of the invention, the method of processing a cerebrovascular medical image further comprises applying bias correction and skull stripping to the MRA image prior to the segmentations.

In an embodiment of the invention, the adjusting of the MRA image comprises analysing the MRA image using a 3D connectivity analysis based on the first and second prior appearance features and the current appearance futures.

In an embodiment of the invention, the adjusting the MRA image is conducted using a Random Forest model.

In an embodiment of the invention, the blood vessels comprise small and large blood vessels.

In an embodiment of the invention, the MRA image of a cerebrovascular tissue is related to a mammalian.

In an embodiment of the invention, the mammalian is a human.

It is also an object of the present invention to provide a system for processing a cerebrovascular medical image, the system comprising a data input interface for receiving a magnetic resonance angiography (MRA) image associated with a cerebrovascular tissue comprising blood vessels and brain tissues other than blood vessels, at least one processor for processing the received MRA image, the MRA image processing comprising segmenting the MRA image using a prior appearance model for generating first prior appearance features representing a first-order prior appearance model and second appearance features representing a second-order prior appearance model of the cerebrovascular tissue, wherein the current appearance model comprises a 3D Markov-Gibbs Random Field (MGRF) having a 2D rotational and translational symmetry such that the MGRF model is 2D rotation and translation invariant; segmenting the MRA image using a current appearance model for generating current appearance features distinguishing the blood vessels from the other brain tissues; adjusting the MRA image using the first and second prior appearance features and the current appearance futures; and generating an enhanced MRA image based on said adjustment.

In an embodiment of the invention, the prior appearance model uses interaction parameters analytically estimated from a set of MRA training data.

In an embodiment of the invention, t the first prior appearance features representing a first-order prior appearance model and the second appearance features representing a second-order prior appearance model are respectively provided by energies of the training data according to the following equations:

$$E_0(z) = \sum_{q=0}^{Q-1} F_{0,vasc}(q; z)[F_{0,vasc}(q; z) - 1]$$

$$E_v(z) = \sum_{q=0}^{Q-1} \sum_{q'=0}^{Q-1} F_{v,vasc}(q; q'; z)[F_{v,vasc}(q; q'; z) - 1]$$

wherein, $E_0$ and $E_v$: variances of the co-occurrence distributions and will be used as a discriminatory features that represent the first order and second-order prior appearance model of cerebral vasculature $F_{0,vasc}$: marginal empirical distributions of gray levels $F_{v,vasc}$: gray level co-occurrences and describe now all the cerebral vasculature from the training set.

In an embodiment of the invention, the prior appearance model excludes alignment of the training data.

In an embodiment of the invention, the current appearance model comprises a Linear combination of Discrete Gaussians (LCDG) model and an EM-based model for linear combination of Gaussian approximation.

In an embodiment of the invention, generating current appearance features comprises estimating first Gibbs probability densities of voxels to be blood vessels ((P (q Vessels))) and estimating second Gibbs probability densities of voxels to be brain tissues other than blood vessels ((P (q Brain))) according to the following equations respectively and making probabilistic decisions based on said first and second calculated Gibbs probability densities.

$$P(q \mid \text{Brain}) = \frac{1}{\alpha}\sum_{r=1}^{2} wp, r\psi(q \mid \theta p, r) - \sum_{l=1}^{C_n} w_{n,l}\psi(q \mid \theta_{n,l})$$

$$P(qVessels) = \frac{1}{1-\alpha}\sum_{r=3}^{C_p} wp, r\psi(q \mid \theta p, r) - \sum_{l=1}^{C_n} w_{n,l}\psi(q \mid \theta_{n,l})$$

$$\text{Where } \alpha = \frac{wp, 1 + wp, 2}{\sum_{r} w_{p,r}}$$

and wherein $C_p$, $C_n$, $w_p$, $w_n$, $\theta_p$, $\theta_n$ denotes the parameters of the LCDG.

In an embodiment of the invention, the MRA image processing further comprising applying bias correction and skull stripping to the MRA image prior to the segmentations.

In an embodiment of the invention, t the adjusting of the MRA image comprises analysing the MRA image using a 3D connectivity analysis based on the first and second prior appearance features and the current appearance futures.

In an embodiment of the invention, the adjusting the MRA image is conducted using a Random Forest model.

In an embodiment of the invention, the system for processing a cerebrovascular medical image further comprises a display for displaying the enhanced MRA image to a user.

In an embodiment of the invention, the system further comprises a scanner for capturing the MRA image and transmitting it to the data input interface.

BRIEF DESCRIPTION OF THE DRAWINGS

The invention will now be described with reference to the accompanying drawings, which illustrate a preferred embodiment of the present invention without restricting the scope of the invention's concept, and in which.

DETAILED DESCRIPTION

Figure 1:
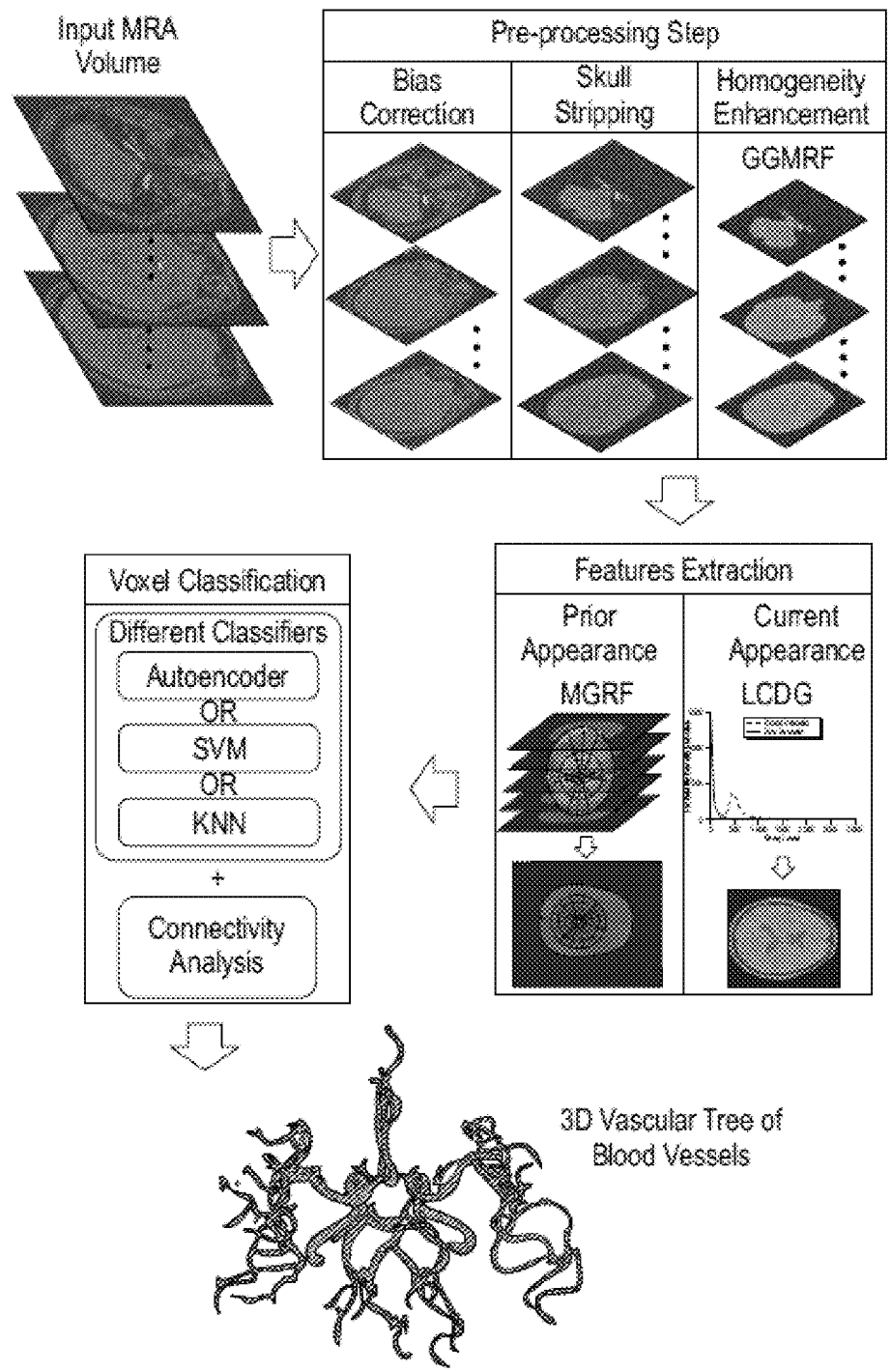
FIG. 1. illustrates the proposed segmentation system.

In accordance with the present invention, a method to extract both micro and macro brain blood vessels from MRA images is proposed. Segmentation of the cerebrovascular structure is crucial since it helps in the diagnoses process, surgery planning, research, and monitoring. Moreover, the benefits of the segmentation of the cerebrovascular structure lay in its ability to improve the simulation of the blood flow and the visualization of the vessels in which each developed method solves a problem faced previously or triggers a specific region of the brain. This present invention proposes a statistical approach, as demonstrated in FIG. 1, that utilizes a voxel-wise classification based on determining probability models of voxel intensities, in order to separate blood vessels from the background of each TOFMRA slice. This is done by approximating the marginal empirical distribution of intensity probabilities with LCDG with alternate signs and utilizing EM-based techniques for linear combination of Gaussian approximation that are adapted for dealing with LCDGs.

The present invention proposes a fully automated method the steps of bias correction and skull stripping, enhancement of vascular contrast and homogeneity, modelling vascular prior appearance using a pairwise, rotation and translation invariant, Markov-Gibbs random field (MGRF), the interaction parameters of which have been analytically estimated from a set of MRA training data, modelling the current appearance using our prior model and a Linear combination of Discrete Gaussians (LCDG) approach, initial classification of vascular tissue using Random Forest, final extraction of the brain vascular system based on 3D connectivity analysis.

The proposed framework performs well in the presence of inhomogeneities that may exist in MRA images. This is due to its encoding local spatial information using the MGRF model to identify vascular tissue irrespective of large-scale variation in absolute signal intensities. Details of the proposed approach are outlined in the following sections.

Let (x, y, z) denote Cartesian coordinates of points in a finite arithmetic lattice R={(x, y, z): x=0, ..., X-1; y=0, ..., Y-1, z=0, ..., Z-1}.

Q={0, ..., Q-1} denotes a set of gray levels.

g: R→Q is a 3D grayscale image.

Bias Correction and Skull Stripping:

Considering bias correction and skull stripping in accordance with an embodiment of the present invention, illumination non-uniformity of infant brain MRIs, which is known as bias field, limits the accuracy of the existing brain extraction approaches. Therefore, to accurately extract the brain it is important to account for the low frequency intensity non-uniformity or inhomogeneity.

Homogeneity Enhancement:

The present invention deals with bias correction and skull stripping. Illumination non-uniformity of infant brain MRIs, which is known as bias field, limits the accuracy of the existing brain extraction approaches. Therefore, to accurately extract the brain it is important to account for the low frequency intensity non-uniformity or inhomogeneity.

Figure 2:
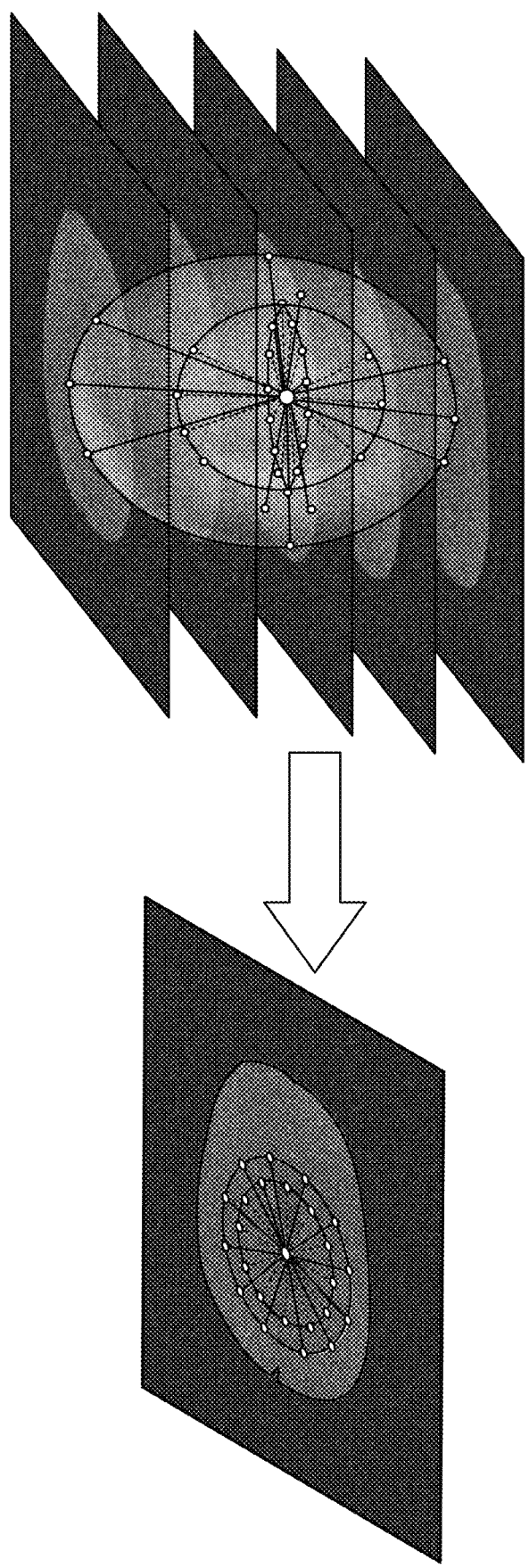
FIG. 2. 2D and 3D illustration of the proposed rotational and translational invariance neighbourhood system.

To enhance the vascular homogeneity, the present invention developed a new 3D generalized Gauss-Markov random field (GGMRF) model with 2D rotational and translational invariance that will be applied after the bias correction and skull striping step. The main idea of the model is to reduce the signals inconsistencies of the MRA data by estimating the new grey level that minimize the Gibbs energy between the voxel of interest and its neighbor. To ensure the proposed GGMRF is invariant under rotations and translations, they selected the neighborhood system to be central-symmetric around the voxel of interest (e.g., spherical-neighborhood system) as demonstrated in FIG. 2. To GGMRF model, let the gray level values of volume g be considered as samples from a 3D GGMRF model with spherically symmetric neighborhood system ($n_1$; $n_2$). The maximum a posteriori (MAP) estimates and voxel-wise stochastic relaxation (iterative conditional mode (ICM) of voxel values at each location s∈R are as follows:

$$q(s) = \mathrm{argmin}|g(s) - q|^\alpha + \rho^\alpha \lambda^\beta \sum_{r \in n_1} \eta_1(r)|g(s+r) - q|^\beta \qquad (1)$$

$$+ \rho^\alpha \lambda^\beta \sum_{r \in n_2} \eta_2(r)|g(s+r) - q|^\beta$$

The neighborhood $n_1$ is located at a unit distance from the central voxel. Similarly, $n_2$ is the neighborhood located at a double unit distance from the central voxel. $\eta_1$ and $\eta_2$ are the corresponding GGMRF potentials, and $\rho$ and $\lambda$ are scaling factors. The parameter $\beta$ [1.01, 2.0] controls the level of smoothing (e.g., $\beta=2$ for smooth vs. $\beta=1.01$ for relatively abrupt edges). The parameter $\alpha$ 1, 2 determines the Gaussian, $\alpha=2$, or Laplace, $\alpha=1$, prior distribution of the estimator.

To enhance the contrast of MRA images, we are proposing to use our former, unsupervised first-order appearance model to estimate the marginal grey level distributions of blood vessels and other brain tissues. The discrete Gaussian (DG) distribution on Q with parameter vector $\theta=(\mu, \sigma^2)$ is defined by its probability mass function.

$$\psi(q|\theta) = \begin{cases} \Phi\dfrac{-0.5-\mu}{\sigma}, & q=0 \\ \Phi\dfrac{(-q-\mu+0.5)}{\sigma} - \Phi\dfrac{(-q-\mu-0.5)}{\sigma}, & 0<q<Q-1 \\ 1 - \Phi\dfrac{(Q-\mu-1.5)}{\sigma}, & q=Q-1 \end{cases} \qquad (2)$$

where $\Phi$ is the standard normal distribution function. An LCDG model with K of dominant modes is given by a sum of $C_p$ positively weighted and $C_n$ negatively weighted discrete Gaussian components with $C_p \geq K$:

$$P(q) = \sum_{r=1}^{C_p} w_{p,r} \psi(q|\theta_{p,r}) - \sum_{l=1}^{C_n} w_{n,l} \psi(q|\theta_{n,l}) \qquad (3)$$

where the weights are constrained to be nonnegative and satisfy $$\sum_{r=1}^{C_p} w_{p,r} - \sum_{l=1}^{C_n} w_n, l = 1 \qquad (4)$$

In the case of TOF-MRA images, K=3, corresponding to grey matter, white matter, and blood vessels. Given the observed voxel intensities within the brain in one slice of an MRA volume, the parameters of the LCDG ($C_p$, $C_n$, $w_p$, $w_n$, $\theta_p$, $\theta_n$) were estimated using the modified expectation-maximization algorithm in [?]. Assuming the positively weighted DG components are ordered such that $\mu_{p,1} \leq \mu_{p,2} \leq \ldots \leq \mu_{p,C_p}$, the marginal distribution of grey levels within brain tissue (grey/white matter) and within blood vessels were calculated as:

$$P(q \mid \text{Brain}) = \frac{1}{\alpha} \sum_{r=1}^{2} wp, r\psi(q \mid \theta p, r) - \sum_{l=1}^{C_n} w_{n,l}\psi(q \mid \theta_{n,l}) \quad (5)$$

$$P(q\text{Vessels}) = \frac{1}{1-\alpha} \sum_{r=3}^{C_p} wp, r\psi(q \mid \theta p, r) - \sum_{l=1}^{C_n} w_{n,l}\psi(q \mid \theta_{n,l})$$

$$\text{Where } \alpha = \frac{wp, 1 + wp, 2}{\sum_r w_{p,r}}$$

Given these preliminaries, we employed the following algorithm to improve the homogeneity and contrast of MRA images as follows:
1) Choose $\delta > 0$
2) For each MRA volume g: R→Q
   a) For each slice $g_i \subset g$
      i) Estimate parameters of the LCDG model using modified EM algorithm.
      ii) Calculate the empirical marginal distri-butions of brain tissue $P_i$(q Brain) and blood vessels $P_i$ (q Vessel) using equation 5

→R b) Initialize contrast-enhanced image E: R
   c) For each s∈R
      i) Solve equation 1 for q(s) using gradient descent
      ii) $P_v \leftarrow P_i([q(s)+0.5] \mid \text{Vessel})$, where [•] denotes the greatest integer function.
      iii) $P_o \leftarrow P_i([q(s)+0.5] \mid \text{Brain})$
      iv) If $P_v \geq P_i$ $E(s) \leftarrow \hat{q}(s) + \delta$ Else $E(s) \leftarrow \hat{q}(s) - \delta$ Note that δ is a "small" value controlling the degree of contrast enhancement; in all our experiments we used δ=1.

Rotation and Translation Invariant MGRF-Based Prior Cerebral Vasculature Appearance Model:

To develop the proposed learnable MGRF model in away that it does not require any alignment stage in order to use it to extract cerebral vasculature. The appearance of cerebral vasculature is modeled 3D MGRF, having 2D rotational and translational symmetry, with neighborhood system N. As illustrated in Fig.?, N is specified by a set of characteristic voxel neighborhoods of the origin, $\{n_v: v=1, 2, \ldots, N\}$ and their corresponding Gibbs potentials $V_v$. A characteristic neighborhood $n_v$ is spherically symmetric if and only if it comprises all voxels whose distance from the origin falls within a half-open interval, $n_v = \{r: d_{min,v} \leq \|r\| < d_{max,v}\}$.

Since the MRA appearance of the cerebral vasculature changes from large vessels (bright) to microvessels (less bright), we have to take this effect into account in order to accurately segment cerebral vasculature. To accomplish this we developed the 3D interaction system to be a function in the z (inferior-superior) direction. That is, for each axial slice of the MRA volume there is a corresponding set of Gibbs interaction potentials $V_v$ (q, q'; z), as well as a gray level potential $V_0(q, q'; z) = V_0(q; z)$. Note that $V_0$ represents the estimated potential for the first order prior appearance of the cerebral vasculature and $V_v$ is the pairwise, or second order, prior appearance of the cerebral vasculature.

To identify/learn the proposed MGRF model, we have to estimate the potentials $V_v$ and $V_0$. Thus, consider a training set of MRA volumes $g = g_1 \ldots g_T$ and the families of voxel pairs (s, s') where s R, s'=s+r, and r $n_v$. Let $F_{v,t}(q, q'; z)$ be a joint empirical probability distribution of gray level co-occurrences in the training nodules from the image $g_t$. Also define $F_{0,t}(q, q'; z) = F_{0,t}(q; z)$ the empirical distribution of gray levels.

The MGRF model of the t-th object is specified by the joint Gibbs probability distribution on the sublattice $R_t = \{s \in R \mid g_t(s) \text{ is vasculature}\}$.

$$P_t(q, q') = \frac{1}{Z_t} \exp\left[|R_t| \sum_{v=0}^{N} \left(\rho v, t \sum_{Z=1}^{Z_t-1} V_{v,t}(q, q'; z F_{v,t}(q, q'; z)\right)\right] \quad (6)$$

where $\rho_{v,t}$ is the average cardinality of the neighborhood $n_v$ with respect to the sublattice $R_t$. We make the simplifying assumption that different vascular trees have approximately the same total volume, $R_t = R_{vasc}$, and the same neighborhood sizes, $\rho_{v,t} = \rho_v$. For independent samples, the joint probability distribution of gray values for all the training cerebral vasculature is as follows:

$$P_S = \frac{1}{Z} \exp\left[TR_{vasc} \sum_{v=0}^{N} \left[\rho_v \sum_{Z=1}^{Z-1} V_{v,vasc}(q, q'; z) F_{v,vasc}(q, q'; z)\right]\right] \quad (7)$$

Where the marginal empirical distributions of gray levels $F_{0,vasc}$ and gray level co-occurrences $F_{v,vasc}$ describe now all the cerebral vasculature from the training set. Using the analytical approach similar to that in previous work, the potentials are approximated with the scaled centered empirical probabilities:

$$V_0, vasc(q; z) = F_0, vasc(q; z) - 1/Q \quad (8)$$

$$V_{v,vasc}(q, q'; z) = F_{v,vasc}(q, q'; z) - \frac{1}{Q^2}$$

For computing MGRF energies $E_0$ and $E_v$ of the spherically symmetric pairwise voxel interactions in the training data, note that the energies are equal to the variances of the co-occurrence distributions:

$$E_0(z) = \sum_{v=0}^{Q-1} F_{0,vasc}(q, z)[F_{0,vasc}(q; z) - 1] \quad (9)$$

$$E_v(z) = \sum_{q=0}^{Q-1} \sum_{q'=0}^{Q-1} F_{0,vasc}(q, z)[F_{0,vasc}(q; z) - 1] \quad (10)$$

The calculated Energies from Eqs (9 and 10) will be used as a discriminatory features that represent the first-order and second-order prior appearance model of cerebral vasculature.

LCDG-Based Current Appearance Model:

The visual appearance of cerebral vasculature in each current data set g to be segmented typically differ from the appearance of the training cerebral vasculature due to non-linear intensity variations from different data acquisition systems and changes in patient tissue characteristics, scanner type, and scanning parameters. This is why, in addition to the appearance prior learned from the normalized training data sets, we model the marginal gray level distribution with a dynamic mixture of two distributions for brain blood vessels and other brain tissues, respectively by using the LCDG model in Eq. 5 to estimate the marginal density of blood vessels and other brain tissues.

Extraction of the Cerebral Vasculature:

To highlight the advantages that the extracted features by using the proposed segmentation approach are separable and it can be accurately classified/segmented by any classifier algorithm, they will feed the extracted prior appearance features and current appearance features to different classifier such as Support Vector Machine, Neural Network, auto-encoder network followed by Softmax decision network, and decision tree. Finally, to extract the cerebral vasculature Matlab toolbox will be used to extract the largest connected 3D component from the initially classified 3D data. To summarize, the whole segmentation approach is as follows; 1) Read TOF MRA volume, 2) Apply bias correction algorithm followed by skull stripping algorithm 3) Use Eqs. 9 and 10 to estimate the energy of the first-order and second-order prior appearance. 3) Use Eq. 5 to estimate the probability density for any voxel to be blood vessels (P (q Vessels)) and probability to be other brain tissues (P (q Brain)), 4) Feed the estimated current and prior features to your classifier. 5) Extract Cerebral Vasculature by Using Matlab tool-box to extract the largest connected component.

Figure 3:
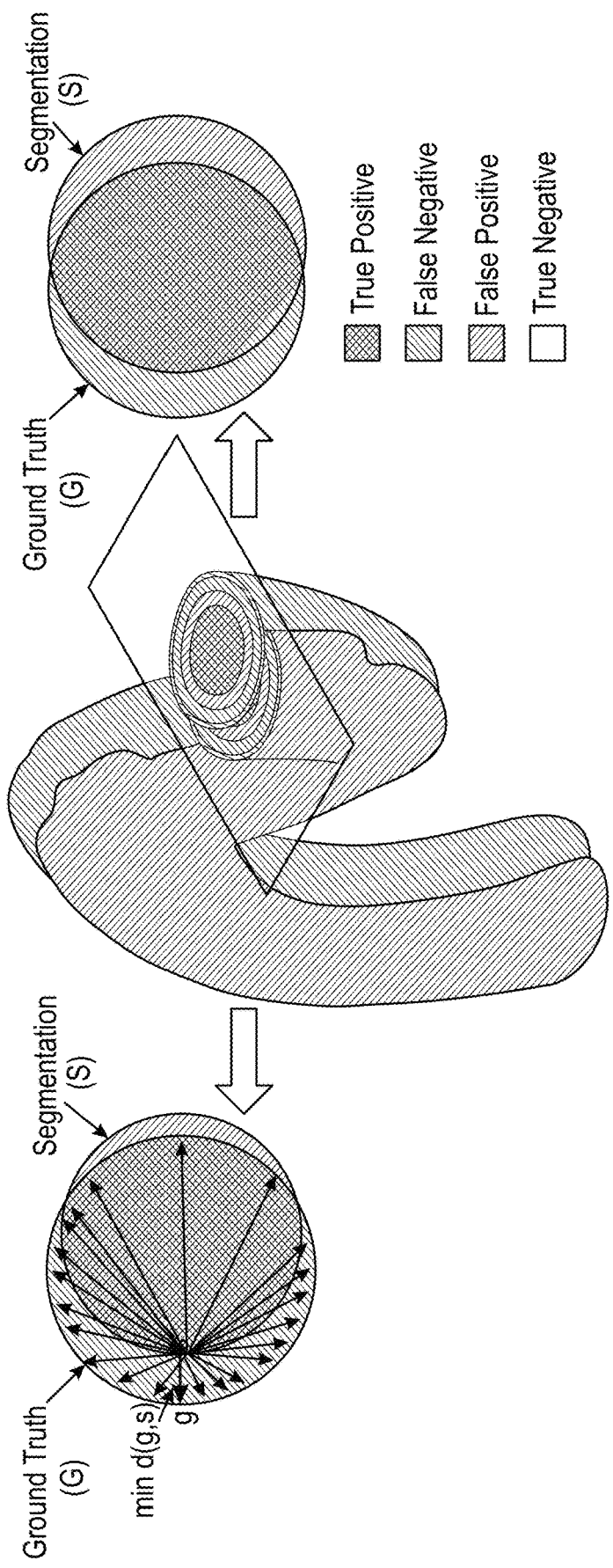
FIG. 3. Illustration of the evaluation metrics (DS) and HD.
Figure 4:
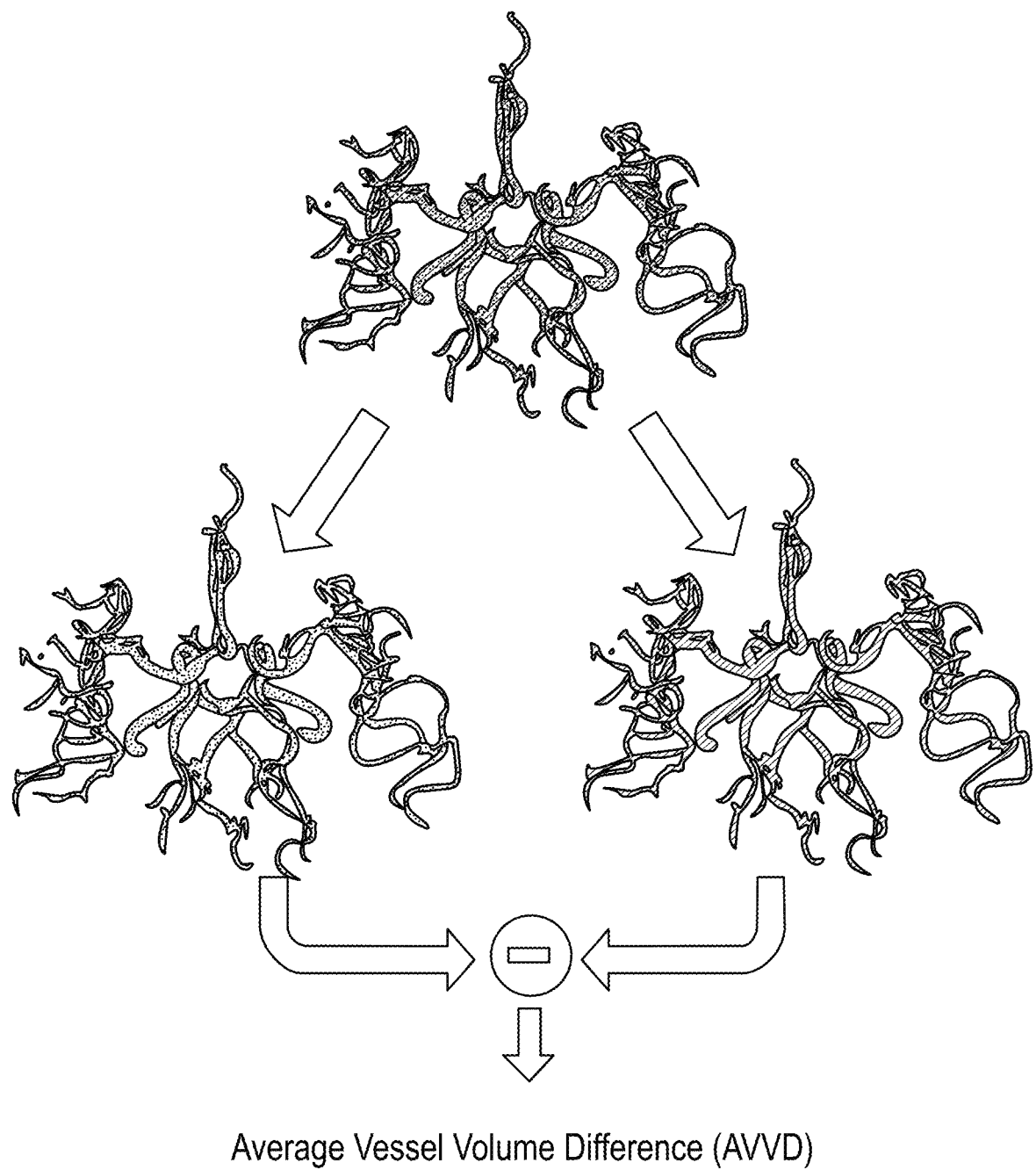
FIG. 4. Illustrates evaluation metrics (DS) and HD (Average Vessel Volume Difference (AVVD))

Evaluation Metrics:

The segmentation results of the proposed blood vessels segmentation framework are evaluated using two types of metrics: area-based similarity metrics and a distance based error. The area-based similarity indicates the overlap between the segmented area and the gold standard. This type of metrics are crucial for studying areal measurements, e.g., total volumes of blood vessels. The distance-based error measures how close edges of the segmented vessels are to the ground truth. In this present invention, the Dice coefficient (DC) and absolute vessels volume difference (AVVD) are used to describe the area-based similarity, while the 95-percentile bidirectional Hausdorff distance (BHD) is used to characterize the distance-based error metric. FIG. 3 is an illustration of the evaluation metrics (DS) and HD and FIG. 4 is the evaluation metrics (DS) and HD.

Dice Coefficient (DC):

The Dice coefficient (DC) is used first to evaluate the segmentation accuracy. DC is the most commonly used similarity metric for segmentation evaluation by characterizing the agreement between the segmented (S) and the gold standard (G) regions based on the determination of true positive (TP) value, true negative (TN) value, false negative (FN) value, and false positive (FP) value. The TP is defined as the number of positively labelled voxels that are correct; the FP is the number of positively labelled voxels that are incorrect; the TN is the number of negatively labelled voxels that are correct; and the FN is the number of negatively labelled voxels that are incorrect.

$$DC = \frac{2 \cdot TP}{2 \cdot TP + FP + FN} \quad (11)$$

The calculated value of the DC can have a percentage value in the range 0% to 100%, where 0% means strong dissimilarity and 100% means that there is a perfect similarity. To obtain the gold standard that used in the segmentation evaluation process, an MRA expert delineated the brain vessels.

Another area-based metric that is used in this paper for the evaluation of segmentation, in addition to the DSC, is the absolute Vessels volume difference (AVVD). The AVVD is the volume difference, (percentage), between the output of the segmentation framework, S, and the gold standard, G, as follow:

$$AVVD(G, S) = \frac{|G - S|}{|G|} \quad (12)$$

where |G−S| is the absolute difference between the number of voxels in G and S, |G| is the number of voxels in G Bidirectional Hausdorff Distance (BHD):

In addition to the DSC and AVVD, the distances between G and S borders are used as an additional metric to measure the accuracy of the segmentation framework. To measure the distance error between the borders of G and S, we used the bidirectional Hausdorff distance (BHD). The HD from the boarder points of G to the boarder points of S is defined as the maximum distance from the border of G to the nearest point on the border of S.

$$HD(G,S) = \max\{\min\{d(g,s)\}\}$$
$$g \in G \; s \in S \quad (13)$$

where g and s denote points of set G and S respectively The bidirectional Haussdorf distance (BHD) between the segmented region S and its ground truth G is defined as:

$$BHD(G,S) = \max\{HD(G,S), HD(S,G)\} \quad (14)$$

In this present invention, they use the 95th-percentile bidirectional Haussdorf distance (BHD) as a metric that measures the segmentation accuracy.

Figure 5A:
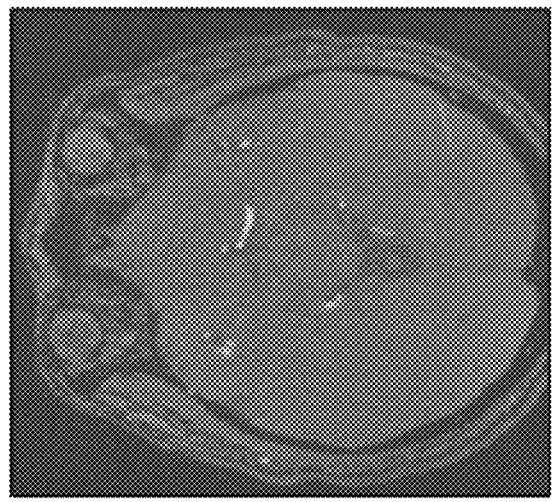
FIG. 5A. 5B. Illustration of the T1-weighted MRI axial views for (a) adult and (b) infant brains.
Figure 5B:
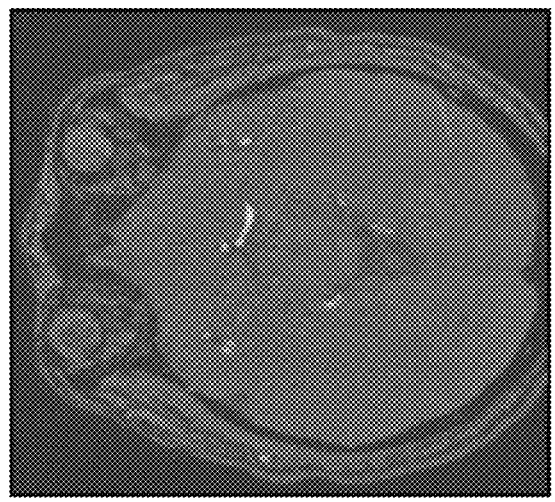

In order to evaluate the performance of the proposed cerebral vasculature segmentation system, it was applied to 270 ToF-MRA data sets which were obtained from the University of Pittsburgh. An MR expert assessed the results qualitatively. The ToF-MRA data were acquired using a 3T Trio TIM scanner with a 12-channel phased-array head coil, resulting in 3-D multislab high-resolution images (160 slices), with a thickness of 0.5 mm, matrix size of 384 448, a flip angle of 15 degrees, repetition time of 21 ms, and echo time of 3.8 ms. In addition, the accuracy of the proposed approach was quantitatively validated using 30 data sets with a known manually segmented ground truth that were obtained by an MR expert. To highlight the role of each step in the proposed segmentation system, the output of each step for a selected axial cross-section of one subject was demonstrated. The homogeneity and contrast is enhanced by using the proposed GGMRF model. Also, to highlight the role of using the current and learned prior appearance model, we displayed the voxel-wise energies for each voxels in ToF-MRA image. It is very clear that the combined energy of each voxel (current and prior appearance) in the cerebral vasculature is higher than the energy of the brain tissues which confirms good guidance for any classifier that we plan to use. Another way to visualize the role of each model for the whole ToF-MRA volume is to use the Maximum Intensity Projection (MIP). FIG. 5 denotes T1-weighted MRI axial views for adult and infant brains.

In conclusion, the cerebral vascular diseases are threatening the life of millions around the world. The diagnosis of such diseases has been a challenge over the years and most physicians would agree that the most important step of recovery is having the right diagnosis. If the illness is precisely identified, most likely proper treatment will be done. Therefore, segmentation of the cerebrovascular structure is crucial since it helps in the diagnoses process, surgery planning, research, and monitoring. Moreover, the benefits of the segmentation of the cerebrovascular structure lay in its ability to improve the simulation of the blood flow and the visualization of the vessels in which each developed method solves a problem faced previously or triggers a specific region of the brain. This invention proposes a statistical approach that utilizes a voxel-wise classification based on determining probability models of voxel intensities, in order to separate blood vessels from the background of each TOFMRA slice. This is done by approximating the marginal empirical distribution of intensity probabilities with LCDG.

It is an object of the present invention to develop a method of processing a cerebrovascular medical image, the method comprising receiving a magnetic resonance angiography (MRA) image associated with a cerebrovascular tissue comprising blood vessels and brain tissues other than blood vessels, segmenting the MRA image using a prior appearance model for generating first prior appearance features representing a first-order prior appearance model and second appearance features representing a second-order prior appearance model of the cerebrovascular tissue, wherein the current appearance model comprises a 3D Markov-Gibbs Random Field (MGRF) having a 2D rotational and translational symmetry such that the MGRF model is 2D rotation and translation invariant, segmenting the MRA image using a current appearance model for generating current appearance features distinguishing the blood vessels from the other brain tissues, adjusting the MRA image using the first and second prior appearance features and the current appearance futures and generating an enhanced MRA image based on said adjustment.

It is also an object of the present invention to provide a method of processing a cerebrovascular medical image, wherein said prior appearance model uses interaction parameters analytically estimated from a set of MRA training data.

In an embodiment, the method of processing a cerebrovascular medical image, wherein the first prior appearance features representing a first-order prior appearance model and the second appearance features representing a second-order prior appearance model are respectively provided by energies of the training data according to the following equations:

$$E_0(z) = \sum_{q=0}^{Q-1} F_{0,vasc}(q, z)[F_{0,vasc}(q; z) - 1]$$

$$E_v(z) = \sum_{q=0}^{Q-1}\sum_{q'=0}^{Q-1} F_{v,vasc}(q, q'; z)[F_{v,vasc}(q, q'; z) - 1]$$

wherein,
$E_0$ and $E_v$: variances of the co-occurrence distributions and will be used as a discriminatory features that represent the first order and second-order prior appearance model of cerebral vasculature
$F_{0,vasc}$: marginal empirical distributions of gray levels
$F_{v,vasc}$: gray level co-occurrences and describe now all the cerebral vasculature from the training set.

In an embodiment, the method of processing a cerebrovascular medical image, wherein said prior appearance model excludes alignment of the training data. This being said, the model does not require an alignment stage.

In an embodiment, the method of processing a cerebrovascular medical image, wherein said current appearance model comprises a Linear combination of Discrete Gaussians (LCDG) model and an EM-based model for linear combination of Gaussian approximation.

In another embodiment, the method of processing a cerebrovascular medical image, wherein said generating current appearance features comprises estimating first Gibbs probability densities of voxels to be blood vessels (P (q Vessels)) and estimating second Gibbs probability densities of voxels to be brain tissues other than blood vessels (P (q Brain)) according to the following equations respectively and making probabilistic decisions based on said first and second calculated Gibbs probability densities:

$$P(q \mid \text{Brain}) = \frac{1}{\alpha}\sum_{r=1}^{2} wp, r\psi(q \mid \theta p, r) - \sum_{l=1}^{C_n} w_{n,l}\psi(q \mid \theta_{n,l})$$

$$P(qVessels) = \frac{1}{1-\alpha}\sum_{r=3}^{C_p} wp, r\psi(q \mid \theta p, r) - \sum_{l=1}^{C_n} w_{n,l}\psi(q \mid \theta_{n,l})$$

$$\text{Where } \alpha = \frac{wp, 1 + wp, 2}{\sum_r w_{p,r}}$$

wherein $C_p$, $C_n$, $w_p$, $w_n$, $\theta_p$, $\theta_n$ denotes the parameters of the LCDG.

In an embodiment, the method of processing a cerebrovascular medical image, further comprising applying bias correction and skull stripping to the MRA image prior to the segmentations.

In an embodiment, the method of processing a cerebrovascular medical image, wherein the adjusting of the MRA image comprises analysing the MRA image using a 3D connectivity analysis based on the first and second prior appearance features and the current appearance futures.

In an embodiment, the method of processing a cerebrovascular medical, wherein the adjusting the MRA image is conducted using a Random Forest model.

In an embodiment, the method of processing a cerebrovascular medical image, wherein the blood vessels comprise small and large blood vessels.

In an embodiment, the method of processing a cerebrovascular medical, wherein said MRA image of a cerebrovascular tissue is related to a mammalian.

In an embodiment, the method of processing a cerebrovascular medical image, wherein said mammalian is a human.

It is also an object of the present invention to provide a system for processing a cerebrovascular medical image, the system comprising a data input interface for receiving a magnetic resonance angiography (MRA) image associated with a cerebrovascular tissue comprising blood vessels and brain tissues other than blood vessels, at least one processor for processing the received MRA image, the MRA image processing comprising segmenting the MRA image using a prior appearance model for generating first prior appearance features representing a first-order prior appearance model and second appearance features representing a second-order prior appearance model of the cerebrovascular tissue, wherein the current appearance model comprises a 3D Markov-Gibbs Random Field (MGRF) having a 2D rotational and translational symmetry such that the MGRF model is 2D rotation and translation invariant; segmenting the MRA image using a current appearance model for generating current appearance features distinguishing the blood vessels from the other brain tissues; adjusting the MRA image using the first and second prior appearance features and the current appearance futures; and generating an enhanced MRA image based on said adjustment.

In an embodiment, the system for processing a cerebrovascular medical image, wherein the adjusting the MRA image is conducted using a Random Forest model.

In an embodiment, the system for processing a cerebrovascular medical image, further comprising a display for displaying the enhanced MRA image to a user.

In another embodiment, the system comprises a scanner to capture an MRA image and send it to the data input interface.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A method of processing a cerebrovascular medical image, the method comprising:
   receiving a magnetic resonance angiography (MRA) image associated with a cerebrovascular tissue comprising blood vessels and brain tissues other than blood vessels;
   segmenting the MRA image using a prior appearance model for generating first prior appearance features representing a first-order prior appearance model and second appearance features representing a second-order prior appearance model of the cerebrovascular tissue, wherein the current appearance model comprises a 3D Markov-Gibbs Random Field (MGRF) having a 2D rotational and translational symmetry such that the MGRF model is 2D rotation and translation invariant;
   segmenting the MRA image using a current appearance model for generating current appearance features distinguishing the blood vessels from the other brain tissues;
   adjusting the MRA image using the first and second prior appearance features and the current appearance futures; and
   generating an enhanced MRA image based on said adjustment.

2. The method of processing a cerebrovascular medical image according to claim 1, wherein said prior appearance model uses interaction parameters analytically estimated from a set of MRA training data.

3. The method of processing a cerebrovascular medical image according to claim 2, wherein the first prior appearance features representing a first-order prior appearance model and the second appearance features representing a second-order prior appearance model are respectively provided by energies of the training data according to the following equations:

$$E_0(z) = \sum_{q=0}^{Q-1} F_{0,vasc}(q, z)[F_{0,vasc}(q; z) - 1]$$

$$E_v(z) = \sum_{q=0}^{Q-1} \sum_{q'=0}^{Q-1} F_{v,vasc}(q, q'; z)[F_{v,vasc}(q, q'; z) - 1]$$

wherein:
$E_0$: variance of a co-occurrence distribution representing the first order prior appearance model;
$E_v$: variance of a co-occurrence distribution representing the second order prior appearance model;
$F_{0,vasc}$: marginal empirical distributions of gray levels;
$F_{v,vasc}$: gray level co-occurrences.

4. The method of processing a cerebrovascular medical image according to claim 3, wherein said prior appearance model excludes alignment of the training data.

5. The method of processing a cerebrovascular medical image according to claim 4, wherein said current appearance model comprises a Linear combination of Discrete Gaussians (LCDG) model and an EM-based model for linear combination of Gaussian approximation.

6. The method of processing a cerebrovascular medical image according to claim 5, wherein said generating current appearance features comprises estimating first Gibbs probability densities of voxels to be blood vessels (P (q Vessels)) and estimating second Gibbs probability densities of voxels to be brain tissues other than blood vessels (P (q Brain)) according to the following equations respectively and making probabilistic decisions based on said first and second calculated Gibbs probability densities:

$$P(q | \text{Brain}) = \frac{1}{\alpha} \sum_{r=1}^{2} wp, r\psi(q | \theta p, r) - \sum_{l=1}^{C_n} w_{n,l}\psi(q | \theta_{n,l})$$

$$P(q \text{Vessels}) = \frac{1}{1-\alpha} \sum_{r=3}^{C_p} wp, r\psi(q | \theta p, r) - \sum_{l=1}^{C_n} w_{n,l}\psi(q | \theta_{n,l})$$

$$\text{Where } \alpha = \frac{wp, 1 + wp, 2}{\sum_r w_{p,r}}$$

and wherein $C_p$, $C_n$, $w_p$, $w_n$, $\theta_p$, $\theta_n$ denotes parameters of the LCDG.

7. The method of processing a cerebrovascular medical image according to claim 6, further comprising applying bias correction and skull stripping to the MRA image prior to the segmentations.

8. The method of processing a cerebrovascular medical image according to claim 7, wherein the adjusting of the MRA image comprises analysing the MRA image using a 3D connectivity analysis based on the first and second prior appearance features and the current appearance futures.

9. The method of processing a cerebrovascular medical image according to claim 8, wherein the adjusting the MRA image is conducted using a Random Forest model.

10. The method of processing a cerebrovascular medical image according to claim 1, wherein the blood vessels comprise small and large blood vessels.

11. The method of processing a cerebrovascular medical image according to claim 1, wherein said MRA image of a cerebrovascular tissue is related to a mammalian.

12. The method of processing a cerebrovascular medical image according to claim 11, wherein said mammalian is a human.

13. The system for processing a cerebrovascular medical image according to claim 1, further comprising a display for displaying the enhanced MRA image to a user.

14. A system for processing a cerebrovascular medical image, the system comprising:
a data input interface for receiving a magnetic resonance angiography (MRA) image associated with a cerebrovascular tissue comprising blood vessels and brain tissues other than blood vessels;
at least one processor for processing the received MRA image, the MRA image processing comprising:
segmenting the MRA image using a prior appearance model for generating first prior appearance features representing a first-order prior appearance model and second appearance features representing a second-order prior appearance model of the cerebrovascular tissue, wherein the current appearance model comprises a 3D Markov-Gibbs Random Field (MGRF) having a 2D rotational and translational symmetry such that the MGRF model is 2D rotation and translation invariant;
segmenting the MRA image using a current appearance model for generating current appearance features distinguishing the blood vessels from the other brain tissues;
adjusting the MRA image using the first and second prior appearance features and the current appearance futures; and
generating an enhanced MRA image based on said adjustment.

15. The system for processing a cerebrovascular medical image according to claim 14, wherein said prior appearance model uses interaction parameters analytically estimated from a set of MRA training data.

16. The system for processing a cerebrovascular medical image according to claim 15, wherein the first prior appearance features representing a first-order prior appearance model and the second appearance features representing a second-order prior appearance model are respectively provided by energies of the training data according to the following equations:

$$E_0(z) = \sum_{q=0}^{Q-1} F_{0,vasc}(q, z)[F_{0,vasc}(q; z) - 1]$$

$$E_v(z) = \sum_{q=0}^{Q-1}\sum_{q'=0}^{Q-1} F_{v,vasc}(q, q'; z)[F_{v,vasc}(q, q'; z) - 1]$$

wherein:
$E_0$: variance of a co-occurrence distribution representing the first order prior appearance model;
$E_v$: variance of a co-occurrence distribution representing the second order prior appearance model;
$F_{0,vasc}$: marginal empirical distributions of gray levels;
$F_{v,vasc}$: gray level co-occurrences.

17. The system for processing a cerebrovascular medical image according to claim 16, wherein said prior appearance model excludes alignment of the training data.

18. The system for processing a cerebrovascular medical image according to claim 17, wherein said current appearance model comprises a Linear combination of Discrete Gaussians (LCDG) model and an EM-based model for linear combination of Gaussian approximation.

19. The system for processing a cerebrovascular medical image according to claim 18, wherein said generating current appearance features comprises estimating first Gibbs probability densities of voxels to be blood vessels (P (q Vessels)) and estimating second Gibbs probability densities of voxels to be brain tissues other than blood vessels (P (q Brain)) according to the following equations respectively and making probabilistic decisions based on said first and second calculated Gibbs probability densities:

$$P(q \mid \text{Brain}) = \frac{1}{\alpha}\sum_{r=1}^{2} wp, r\psi(q \mid \theta p, r) - \sum_{l=1}^{C_n} w_{n,l}\psi(q \mid \theta_{n,l})$$

$$P(qVessels) = \frac{1}{1-\alpha}\sum_{r=3}^{C_p} wp, r\psi(q \mid \theta p, r)\sum_{l=1}^{C_n} -w_{n,l}\psi(q \mid \theta_{n,l})$$

Where $\alpha = \dfrac{wp, 1 + wp, 2}{\sum_r w_{p,r}}$ and wherein $C_p$, $C_n$, $w_p$, $w_n$, $\theta_p$, $\theta_n$ denotes the parameters of the LCDG.

20. The system for processing a cerebrovascular medical image according to claim 19, wherein the MRA image processing further comprising applying bias correction and skull stripping to the MRA image prior to the segmentations.

21. The system for processing a cerebrovascular medical image according to claim 20, wherein the adjusting of the MRA image comprises analysing the MRA image using a 3D connectivity analysis based on the first and second prior appearance features and the current appearance futures.

22. The system for processing a cerebrovascular medical image according to claim 21, wherein the adjusting the MRA image is conducted using a Random Forest model.

* * * * *